(12) United States Patent
Bartoli et al.

(10) Patent No.: US 7,010,973 B2
(45) Date of Patent: Mar. 14, 2006

(54) METHOD AND APPARATUS FOR IMPROVING ACCURACY IN ULTRASONIC ECHO RANGING SYSTEMS

(75) Inventors: Daniel George Bartoli, Peterborough (CA); Gabriel Tolciu, Kanata (CA)

(73) Assignee: Siemens Milltronics Process Instruments Inc., Peterborough (CA)

( * ) Notice: Subject to any disclaimer, the term of this patent is extended or adjusted under 35 U.S.C. 154(b) by 0 days.

(21) Appl. No.: 10/804,620

(22) Filed: Mar. 19, 2004

(65) Prior Publication Data

US 2005/0204812 A1   Sep. 22, 2005

(51) Int. Cl.
    *G01F 23/284* (2006.01)
(52) U.S. Cl. .................................................... 73/290 V
(58) Field of Classification Search .............. 73/290 R, 73/290 V
    See application file for complete search history.

(56) References Cited

U.S. PATENT DOCUMENTS

| | | | |
|---|---|---|---|
| 4,596,144 A * | 6/1986 | Panton et al. ................. | 73/620 |
| 6,277,053 B1 * | 8/2001 | Desembrana ................ | 482/11 |
| 6,621,763 B1 * | 9/2003 | Lyon ............................ | 367/99 |
| 6,734,819 B1 * | 5/2004 | Spanke ........................ | 342/124 |
| 2002/0109626 A1 * | 8/2002 | Spanke ........................ | 342/124 |

* cited by examiner

*Primary Examiner*—Hezron Williams
*Assistant Examiner*—Rodney Frank
(74) *Attorney, Agent, or Firm*—Fay, Sharpe, Fagan, Minnich & McKee, LLP

(57) ABSTRACT

A method and apparatus for calibrating and/or improving the accuracy of time of flight ranging or level measurement systems. A correction factor is determined and applied to the calculated receive times for echo pulses in response to a change in the amplitude of the echo pulses or in response to a change in the noise floor.

13 Claims, 4 Drawing Sheets

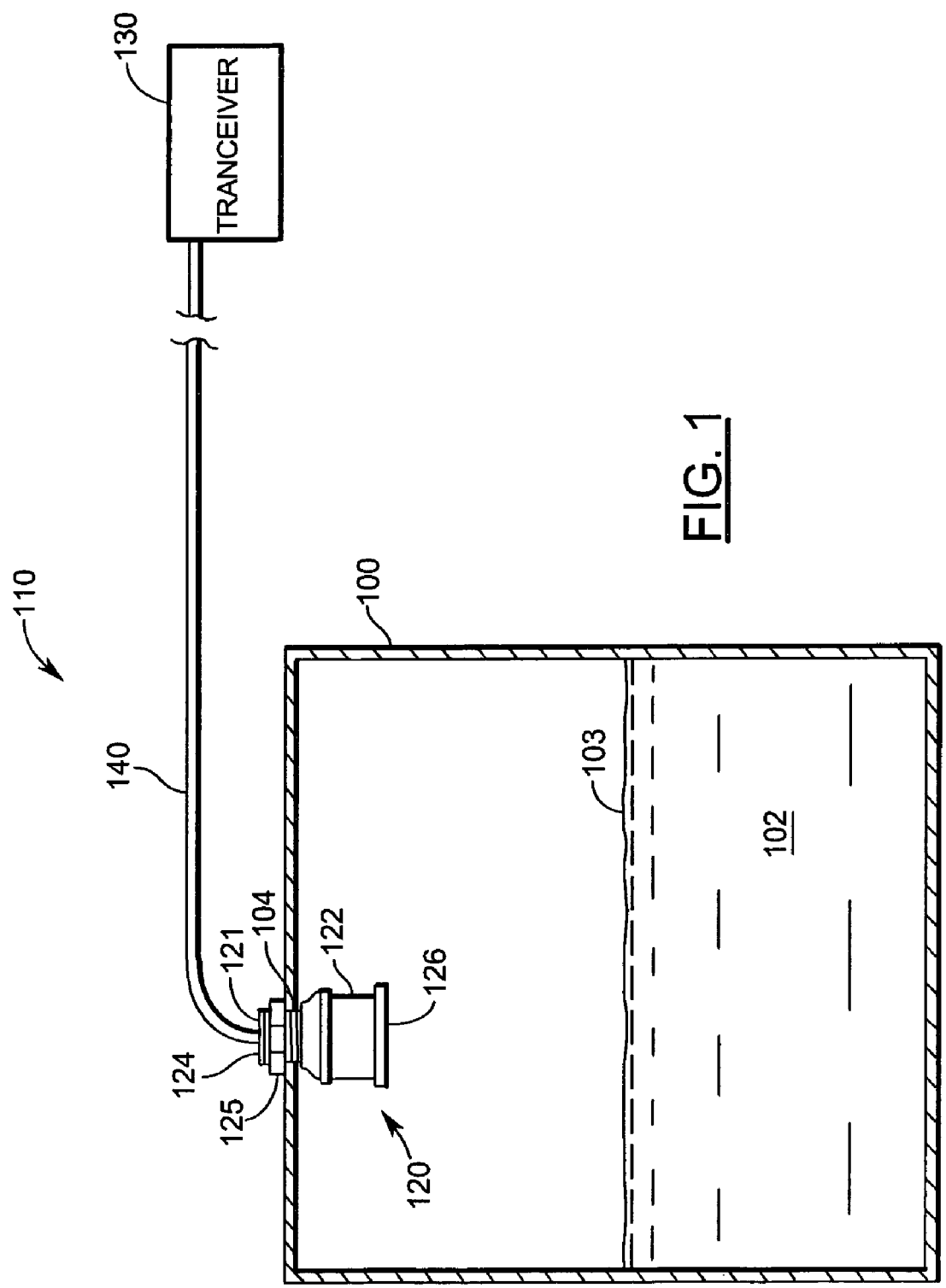

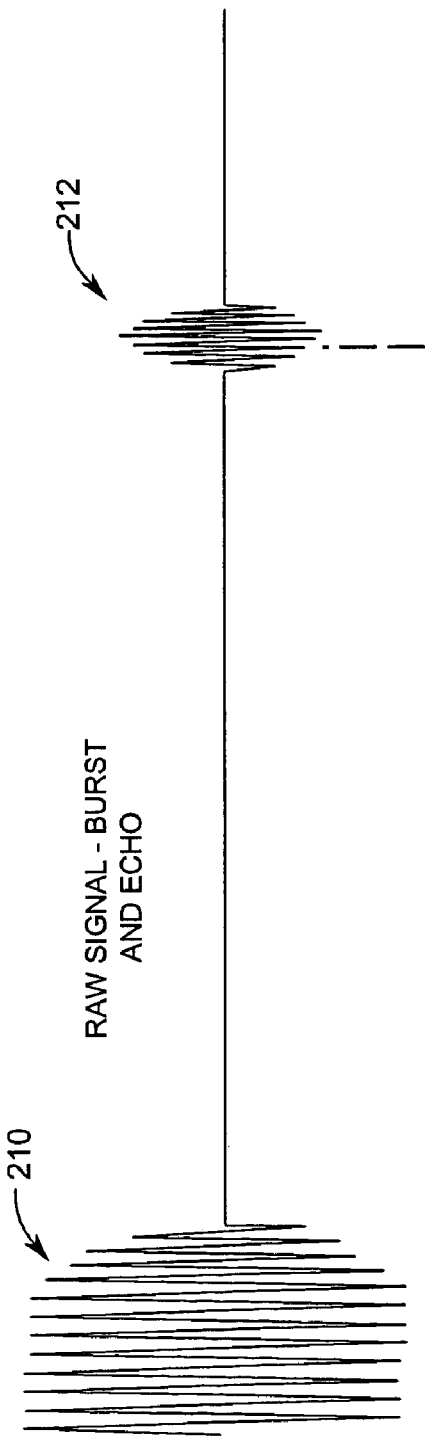
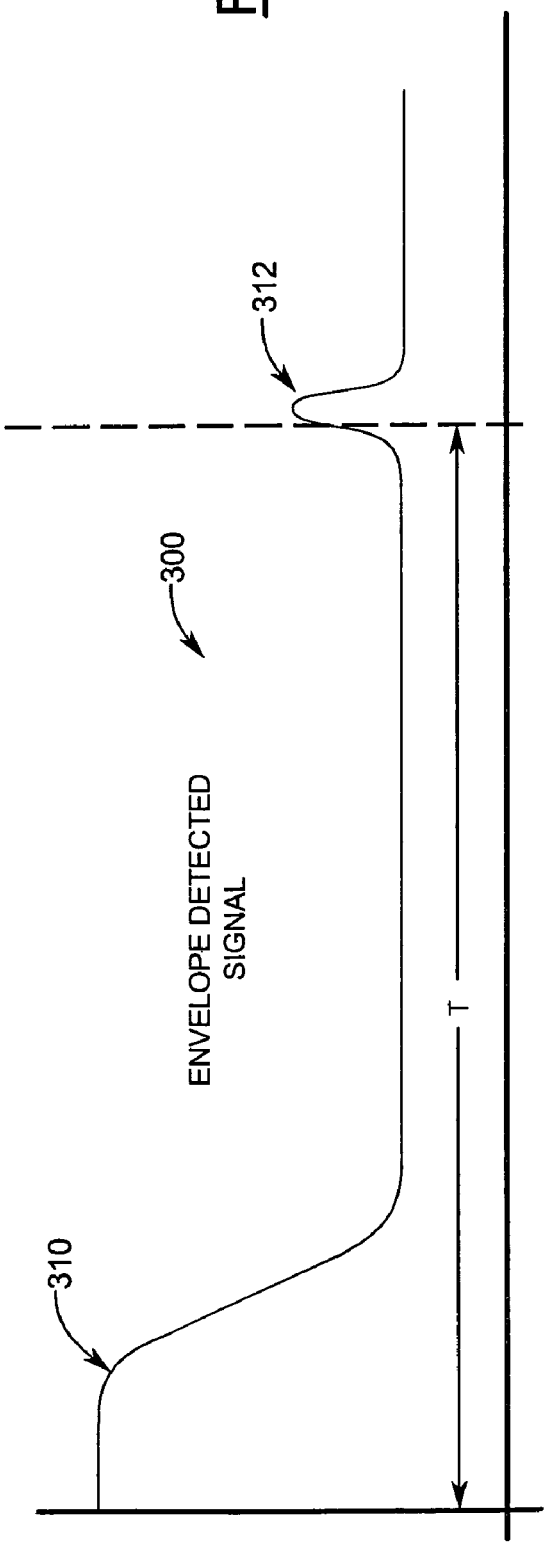

METHOD AND APPARATUS FOR IMPROVING ACCURACY IN ULTRASONIC ECHO RANGING SYSTEMS

FIELD OF THE INVENTION

The present invention relates to time-of-flight ranging systems and level measurement systems, and more particularly to a method for improving the accuracy of an ultrasonic based echo ranging system.

BACKGROUND OF THE INVENTION

Pulse-echo acoustic ranging systems, also known as time-of-flight ranging systems, are commonly used in level measurement applications. Pulse-echo acoustic ranging systems determine the distance or range to a reflector (i.e. reflective surface) by measuring how long after transmission of a burst of energy pulses the echoes or reflected pulses are received. Ultrasonic pulse-echo ranging systems utilize ultrasonic pulses.

To provide accurate level measurements, the reflected or echo pulses need to be precisely detected and processed. Since the amplitude of the echo pulses can vary, the threshold point on the pulse becomes critical for determining accurate timing information. In ultrasonic based level measurement or echo ranging systems, accuracy of the level measurements has been found to decrease significantly with increasing ranging distances.

Accordingly, there remains a need for improvements in the accuracy of ultrasonic based level measurement and echo ranging systems.

BRIEF SUMMARY OF THE INVENTION

The present invention provides a method and/or apparatus for improving accuracy in ultrasonic echo ranging systems.

According to one aspect, the present invention provides a method for providing a reference point on the echo signals in an echo profile for measuring the time of flight of the echo pulse.

In a first aspect, the present invention provides a method for generating an echo profile in a time-of-flight ranging system, the method comprises the steps of: transmitting one or more bursts of energy towards a surface; receiving reflected pulses from the surface, and converting the reflected pulses into an echo profile, the echo profile including an echo pulse; determining a receive time for the echo pulse, the receive time being based on a time reference to a measurement point on the echo pulse, the echo pulses having an amplitude and the measurement point being taken relative to the amplitude; applying a correction to the receive time, wherein the correction is applied in response to a change in the amplitude of the echo pulse, or the noise floor.

In another aspect, the present invention provides a level measurement apparatus for measuring the level of a material contained in a vessel, the level measurement apparatus comprises: a transducer module, the transducer module includes a transducer for transmitting energy pulses in response to application of transmit signals, and the transducer is responsive to receiving energy pulses and converting the received energy pulses into echo signals; a transceiver module for transmitting the transmit signals and receiving the echo signals, and the transceiver module includes processing means for processing the echo signals into an echo profile, the echo profile comprises one or more echo pulses; the processing means includes means for determining a receive time for each of the echo pulses; the processing means includes means for adjusting the receive time for the echo pulses in response to a change in the amplitude of the echo pulses or a change in noise floor; the processing means includes means for calculating a level measurement for the material contained in the vessel, the level measurement is based on the time between the transmission of the energy pulses and the receive time of the echo pulses.

In a further aspect, the present invention provides a method for generating an echo profile in a time-of-flight ranging system, the method comprises the steps of: transmitting an ultrasonic energy burst towards a surface; receiving reflected pulses from the surface, and converting the reflected pulses into an echo profile, the echo profile includes a plurality of echo pulses; determining a receive time for each of echo pulses, said receive time being based on a time reference to a measurement point on the echo pulses, each of the echo pulses having an amplitude and the measurement point being taken relative to the amplitude and noise floor; applying a time correction to the receive time, wherein the correction is applied in response to a change in the echo pulse; the step of applying a time correction includes determining a correction factor $C_f$ as follows:

$$C_f = ((SNRC - SNR/(S_a)) + O_f$$

where: $C_f$=correction factor
$S_a$=slope of an edge on the echo pulse
SNR=signal to noise ratio
SNRC=signal to noise ratio at calibration (dB)
$O_f$=calibrated offset; and adding the correction factor $C_f$ to the receive time.

In yet another aspect, the present invention provides a level measurement device for measuring a distance to a material having a surface, the level measurement device comprises: a transducer for emitting energy pulses and detecting energy pulses reflected by the surface of the material; a controller having a receiver and a transmitter; the transducer includes an input port operatively coupled to the transmitter and is responsive to the transmitter for emitting the energy pulses, and the transducer includes an output port operatively coupled to the receiver for outputting reflected energy pulses coupled by the transducer; the receiver includes a converter for converting the reflected energy pulses into echo signals; the controller includes a program component for generating an echo profile based on the echo signals; the processing means includes a program component for calculating a receive time for each of the echo signals; the processing means includes a program component for adjusting the receive time for the echo signals in response to a change in the amplitude of the echo pulses or a change in noise floor; the processing means includes a program component for calculating a level measurement for the material contained in the vessel, the level measurement is based on the time between the transmission of the energy pulses and the receive time of the echo signals.

Other aspects and features of the present invention will become apparent to those ordinarily skilled in the art upon review of the following description of specific embodiments of the invention in conjunction with the accompanying drawings.

BRIEF DESCRIPTION OF THE DRAWINGS

Reference is now made to the accompanying drawings which show, by way of example, embodiments of the present invention and in which:

FIG. 1 shows in diagrammatic form a time-of-flight or level measurement system suitable for implementing the present invention;

FIG. 2 shows in diagrammatic form a raw signal burst and raw echo signal;

FIG. 3 shows in graphical form a detected envelope signal or echo profile for the raw signal burst and echo of FIG. 2;

In the figures like references indicate like elements or components.

DETAILED DESCRIPTION OF EMBODIMENTS OF THE INVENTION

Figure 4:
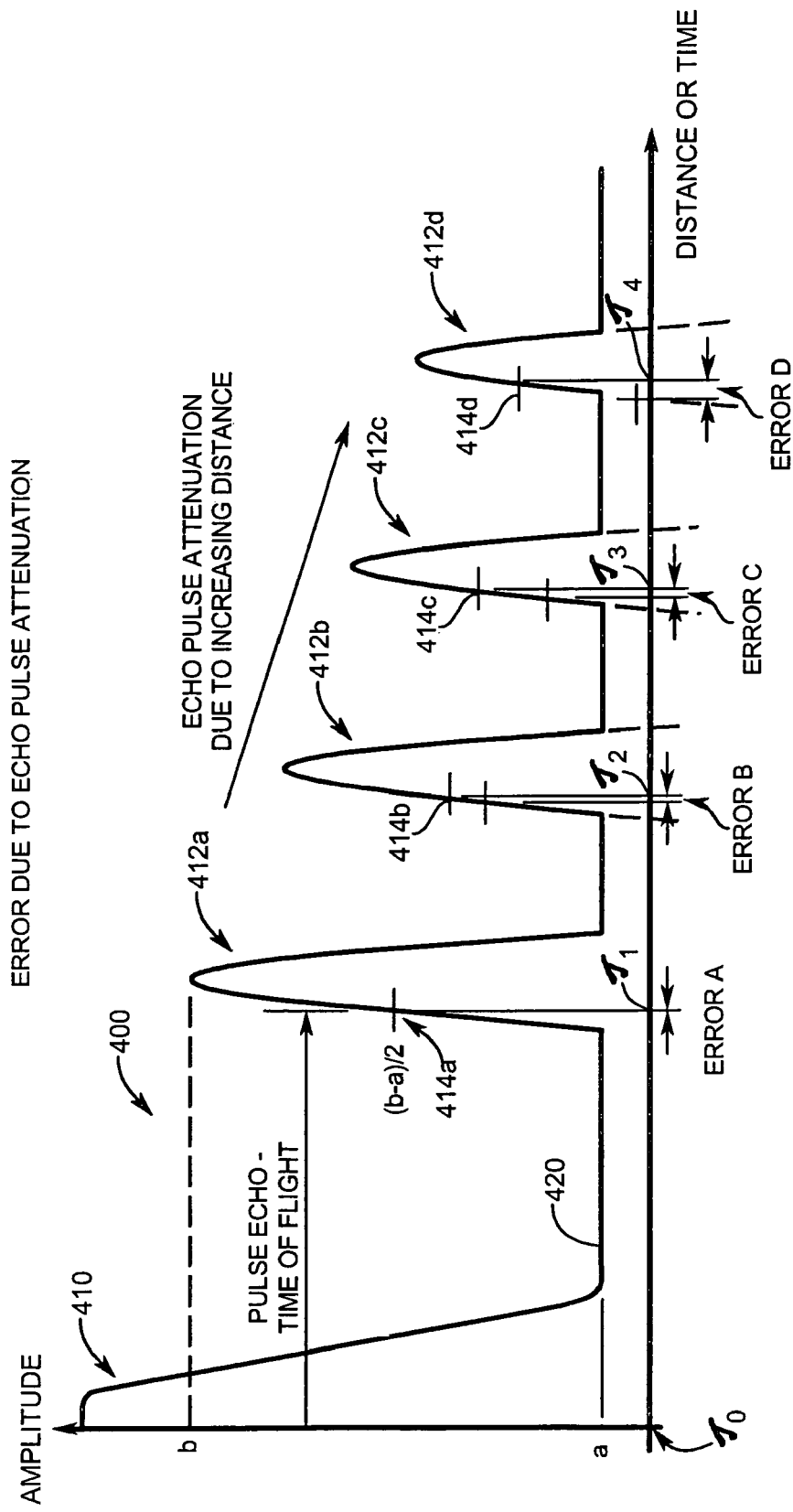
FIG. 4 shows in diagrammatic form an example of error arising from attenuation of echo pulses.

Reference is first made to FIG. 1, which shows in diagrammatic form an echo ranging or level measurement system suitable for implementing the present invention. The echo ranging or level measurement system is indicated generally by reference 110.

The level measurement system 110 provides non-contactive measurement, and is utilized to determine the distance to a surface capable of reflecting energy pulses, for example the surface of a liquid, sludge orgranular material 102 contained in a storage vessel or tank 100 (FIG. 3). The distance, i.e. level measurement of the material 102, is determined by transmitting energy pulse(s) and measuring the time for reflected or echo pulse(s) to be received. The level measurement system 110 according to this aspect utilizes an ultrasonic transducer.

As shown in FIG. 1, the level measurement system 110 comprises an ultrasonic transducer module 120 and a transceiver module 130. The transducer 120 includes an input/output port 121 which is coupled to the transceiver module 130 through a conductor or cable 140. The conductor 140 may comprise a two wire arrangement which provides a link for receiving transmit energy pulses or bursts from the transceiver module 130, and a link for transmitting receive (i.e. echo) energy pulses to the transceiver module 130. The transceiver module 130 includes electronic circuitry and stored-program controlled device(s), e.g. a microprocessor or microcontroller operating under the control of computer code in the form of firmware or software, for processing the echo signals and determining the level measurements, i.e. the distance to the surface of the material 102. These and other techniques associated with level measurement systems will be familiar and within the understanding of those skilled in the art.

The ultrasonic transducer module 120 is mounted in an access port 104 in the top of the storage vessel 100. The vessel 100 holds the material 102 having a level or depth defined by a top surface indicated by reference 103. The surface 103 of the material 102 serves to reflect the ultrasonic energy which is emitted by the ultrasonic transducer module 120.

The ultrasonic transducer module 120 comprises a housing or enclosure 122 and may include a threaded collar 124 and fastener 125 which secures the transducer 120 to the storage tank 100. The ultrasonic transducer 100 is mounted or contained inside the enclosure 122. The ultrasonic housing 122 includes an emitter end indicated by reference 126. The input/output port 121 is coupled to the transceiver module 130 through the conductor cable 140. In response to signals from the transceiver module 130, ultrasonic energy pulses are generated by the ultrasonic transducer 100 and emitted from the end 126 of the transducer module 120 towards the surface 103 of the material 102 contained in the storage vessel 100. Echo pulses reflected by the surface 103 are picked up or received by the ultrasonic transducer 100 and converted into electrical signals or pulses which are transmitted to the transceiver module 130 for further processing and to determine the level or depth of the material 102 in the vessel 100. The level of the material 102 is determined by measuring or determining the time between the transmit pulse from the transceiver 130 to the surface 103 and the reception of the echo pulse back at the transceiver module 130. The receive time is then used to calculate the distance to the surface 103 of the material 102.

The electronic circuitry in the transceiver module 130 (FIG. 1) includes a controller or signal processor unit (e.g. a programmable microprocessor), an analog-to-digital (A/D) converter, a transmitter circuit, a receiver circuit, and a power supply unit. The particular implementation details of the electronic circuitry will be familiar to those skilled in the art. The transducer 120 (FIG. 1) emits a transmit pulse or energy burst, i.e. a raw signal burst 210 as depicted in FIG. 2. The raw signal burst 210 comprises a burst of energy pulses, e.g. ultrasonic pulses, which are emitted or transmitted by the transducer and directed at a surface to be measured. The surface of the material reflects the transmit energy burst and the reflected energy pulses are coupled by the transducer and converted into a raw echo signal 212 as depicted in FIG. 2. The transducer 120 (FIG. 1) serves the dual role of detecting the reflected energy pulses and converting the raw signal echo 212 into electrical signals for processing by the controller unit. The electrical signals corresponding to the raw signal echo 212 are applied to the receiver and sampled and digitized by the A/D converter in the transceiver 130 (FIG. 1). The controller unit or signal processor, for example a microprocessor operating under firmware control, takes the digitized output and generates a detected envelope or echo profile 300 having a form as shown in FIG. 3.

Referring to FIG. 3, the echo profile 300 comprises a half pulse portion 310 which corresponds to the ring-down in the transducer 120 (FIG. 1). The ring-down comprises the period or interval during which the transducer 120 (FIG. 1) is still "ringing down" from the transmit pulses emitted and as such this interval is not considered for detecting reflected energy pulses (i.e. the raw signal echo 212). Following the ring-down, the echo profile 300 comprises one or more echo pulses 312. The echo pulse 312 corresponds to the detected raw signal echo 212 (FIG. 2) and may include further processing by the signal processor.

Reference is next made to FIG. 4, which shows an exemplary echo pulse envelope 400 and the error which arises due to attenuation of the echo pulses. The echo pulse envelope 400 comprises a half or ring-down pulse 410 and a number of echo pulses 412, shown individually as 412a, 412b, 412c and 412d in FIG. 4. The distance to the surface of the material is based on determining the time-of-flight between the transmission of the transmit burst and the reception of the echo signal. Typically, the time-of-flight measurement is taken from the start of the ultrasonic burst to the leading edge of the received echo pulse. A mid-way point on the leading edge of the echo pulse is typically selected for the time reference. As shown in FIG. 4, the start time or $T_0$ is taken at the start of the ring-down pulse 410, and the receive time for the echo pulse 412a is given by a mid-way point 414a. The mid-way point 414a corresponds to a time $T_1$. The mid-way point 414 is defined as the amplitude of the echo pulse 412 that is half-way or 50% between the lowest point (i.e. valley) before the echo pulse and the peak or amplitude value of the pulse.

In practical systems, there will be noise, and the noise is represented as a noise floor level indicated by reference 420 in FIG. 4. The noise floor 420 is taken as the lowest point before the echo pulse 412, which means that the mid-way point 414 is determined as the difference between the amplitude $A_P$ of the echo pulse 412 and the level of the noise floor 420. The noise floor 420 and the amplitude $A_P$ also determine the Signal-to-Noise Ratio or SNR. The SNR is defined as the difference between the amplitude $A_P$ of the echo pulse 412 and the noise floor $N_f$, as follows:

$$SNR = A_P - N_f$$

Where: $A_P$=amplitude (dBuV)
$N_f$=noise floor (dBuV)

Referring still to FIG. 4, the other echo pulses 412b, 412c and 412d experience attenuation due to increasing distance, i.e. between the transducer and the surface of the material to be measured. The attenuation occurs as the echo pulses 412 propagate through air. The mid-way points 414b, 414c and 414d for the echo pulses 412b, 412c and 412d correspond to times $T_2$, $T_3$ and $T_4$, respectively. As a result of this attenuation, the mid-way points 414b, 414c and 414d have shifted up or closer to the peak and this shift has introduced a shift or delay in the respective receive time $T_2$, $T_3$ and $T_4$, which is denoted as Error B, Error C and Error D, respectively. The quantum of the Error B, C, D depends on the slope of the leading edge of the echo pulse 412, and any change in the signal-to-noise ratio or SNR.

Figure 5:
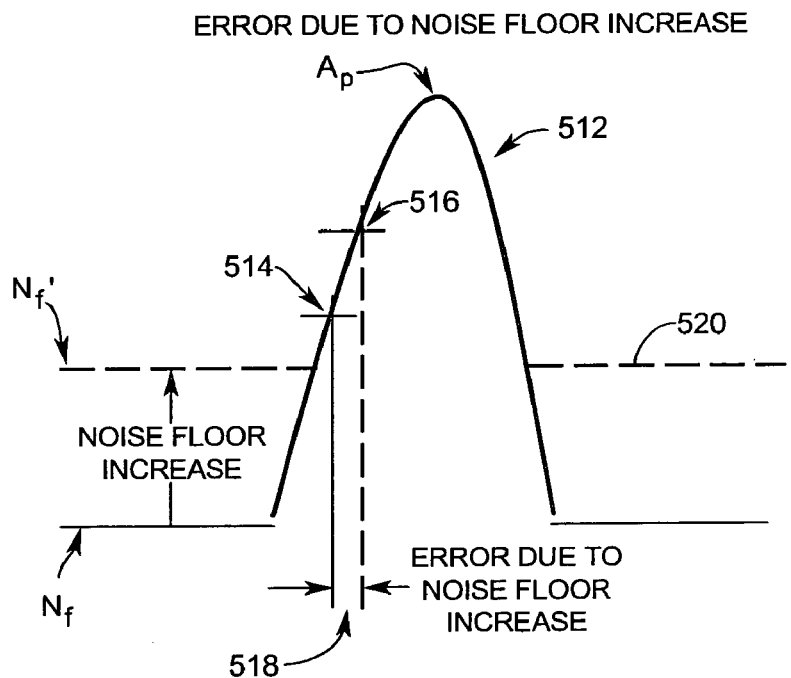
FIG. 5 shows in diagrammatic form an example of error in an echo pulse arising from a noise floor increase.
Figure 6:
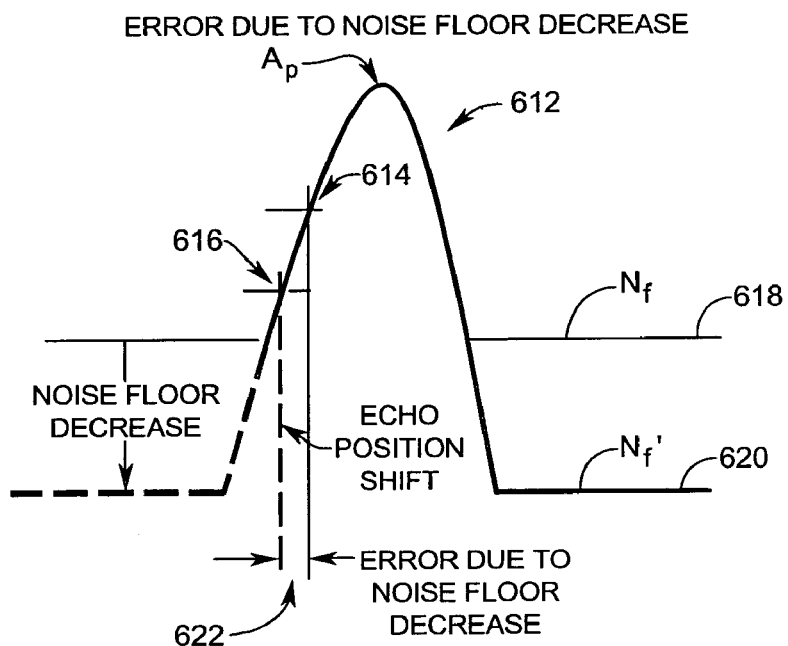
FIG. 6 shows in diagrammatic form an example of error in an echo pulse arising from a decrease in noise floor.

The mid-way point on the echo pulse and the accuracy of the receive time is also affected by changes in the noise floor. Referring to FIG. 5, an echo pulse 512 has a mid-way point 514 for a noise floor $N_f$ or 518. If the noise floor increases to $N_f'$ or 520, then the mid-way point or 50% value shifts to point 516 on the echo pulse 512. The shift of the mid-way point to 516 introduces an error, in this case, a delay in the receive time $T_R$. Similarly, a decrease in the noise floor $N_f$ (as shown in FIG. 6) causes a shift in the mid-way point in the other direction resulting in an earlier receive time $T_R$. Accordingly, a change in the SNR (i.e. defined as the difference between the amplitude A of the echo pulse and the noise floor) from the value the system was originally or previously calibrated at will introduce a shift (i.e. delay or advance) in the receive time for the echo pulse(s).

As shown in FIG. 6, an echo pulse 612 has a mid-way point 614 for a noise floor $N_f$ or 618. If the noise floor decreases or falls to $N_f'$ or 620, then the mid-way point or 50% value shifts to point 616 on the echo pulse 612. The shift of the mid-way point to 616 introduces an error, in this case, an earlier receive time $T_R$. The change in receive $T_R$ is denoted by reference 622.

According to one aspect of the invention, the errors introduced in the echo pulses as described above are corrected by determining a correction factor $C_f$ (seconds) according to the following relationship:

$$C_f((SNRC-SNR)/(S_a)) + O_f$$

Where:
$C_f$=correction factor (seconds)
$S_a$=average slope of leading edge of echo pulse (dB/seconds)
$O_f$=calibrated offset (seconds)
SNR=signal to noise ratio (dB)
SNRC=signal to noise ratio at calibration (dB)

The average slope, SNR and SNRC are determined using processing techniques or steps that will be familiar to those skilled in the art.

According to this aspect, the calibrated offset $O_f$ represents the receive time error measured, for example, during a calibration procedure. The calibrated offset $O_f$ is generated by applying the formula for correction factor to the condition where SNRC−SNR=0 as follows:

$$C_f((SNRC-SNR)/(S_a)) + O_f$$

Then,
hd f=((0)/$S_a$)+$O_f$
$C_f = O_f$

Using the above relationship, a correction factor $C_f$ is calculated for any given SNR, and the correction factor $C_f$ is added to the receive time for the echo pulse (or subtracted from the receive time for a drop in the noise floor), thereby improving the accuracy of the calculated receive time and subsequently the level measurement as determined based on the receive time. In a time-of-flight ranging system or level measurement system, the implementation of the calibration is realized by applying the following equation to the calculated receive time variable:

$$receive\_time\ receive\_time - C_f$$

More specifically, the steps for determining correction factor as described above are implemented in computer or program code as a function or routine in firmware or software, for example as part of the receive time algorithm, executed by the controller in the transceiver module 130 described above with reference to FIG. 1. The implementation details will be within the understanding of one ordinarily skilled in the art.

The present invention may be embodied in other specific forms without departing from the spirit or essential characteristics thereof. Certain adaptations and modifications of the invention will be obvious to those skilled in the art. Therefore, the above-discussed embodiments are considered to be illustrative and not restrictive, the scope of the invention being indicated by the appended claims rather than the foregoing description, and all other changes which come within the meaning and range of equivalency of the claims are therefore intended to be embraced therein.

What is claimed is:

1. A method for generating an echo profile in a time-of-flight ranging system, said method comprising the steps of:
   transmitting one or more bursts of energy towards a surface;
   receiving reflected pulses from said surface, and converting said reflected pulses into an echo profile, said echo profile including an echo signal;
   determining a receive time for said echo signal, said receive time being based on a time reference to a measurement point on said echo signal, said echo signal having an amplitude and said measurement point being taken relative to the amplitude;
   applying a correction to said receive time, wherein said correction is applied in response to a change in the amplitude of said echo signal and said applying comprises determining a signal-to-noise ratio for the change in amplitude and using a slope for an edge of said echo signal to determine a correction factor for said receive time.

2. The method for generating an echo profile as claimed in claim 1, wherein the edge of said echo signal comprises a leading edge, and said correction factor $C_f$ is determined as follows:

$$C_f((SNRC-SNR)/(S_a))$$

Where: $C_f$=correction factor
$S_a$=slope of leading edge of echo pulse
SNR=signal to noise ratio
SNRC=signal to noise ratio at calibration.

3. The method for generating an echo profile as claimed in claim 2, wherein said measurement point is taken at an approximately mid-way point for an echo signal having a. given amplitude, and wherein said correction factor determination includes a calibrated offset $O_f$ as follows:

$$C_f((SNRC-SNR)/(S_a)) + Of.$$

4. The method for generating an echo profile as claimed in claim 3, wherein said signal-to-noise ratio comprises the difference between the amplitude of said echo signal and a noise floor.

5. The method for generating an echo profile as claimed in claim 4, wherein said noise floor is variable, and the amplitude of said echo signal, is subject to attenuation.

6. A level measurement apparatus for measuring the level of a material contained in a vessel, said level measurement apparatus comprising:
  a transducer module, said transducer module including a transducer for transmitting energy pulses in response to application of transmit signals, and said transducer being responsive to receiving energy pulses and converting said received energy pulses into echo signals;
  a transceiver module for transmitting said transmit signals and receiving said echo signals, and said transceiver module including processing means for processing said echo signals into an echo profile, said echo profile comprising one or more echo pulses;
  said processing means including means for determining a receive time for each of said echo pulses;
  said processing means including means for adjusting the receive time for said echo pulses in response to a change in the amplitude of said echo pulses or a change in noise floor and said means for adjusting the receive time comprises means for generating a correction factor, said correction factor being based on a signal-to-noise determination and a slope value for a leading edge of said echo pulse;
  said processing means including means for calculating a level measurement for the material contained in the vessel, said level measurement being based on the time between the transmission of said energy pulses and the receive time of said echo pulses.

7. The level measurement system as claimed in claim 6, wherein said correction factor Cf is determined as follows:

$$C_f = ((SNRC - SNR)/(S_a))$$

Where: Cf=correction factor
$S_a$=average slope of leading edge of echo pulse
SNR=signal to noise ratio
SNRC=signal to noise ratio at calibration.

8. A method for generating an echo profile in a time-of-flight ranging system, said method comprising the steps of:
  transmitting an ultrasonic energy burst towards a surface;
  receiving reflected pulses from said surface, and converting said reflected pulses into an echo profile, said echo profile including a plurality of echo pulses;
  determining a receive time for each of said echo pulses, said receive time being based on a time reference to a measurement point on said echo pulses, each of said echo pulses having an amplitude and said measurement point being taken relative to the amplitude;
  applying a time, correction to said receive time, wherein said correction is applied in response to a change in characteristics of said echo pulse;
  said step of applying a time correction includes determining a correction factor $C_f$ as follows:

$$C_f = ((SNRC - SNR)/(S_a)) + O_f$$

where: $C_f$=correction factor
$S_a$-slope of an edge on said echo pulse
SNR=signal to noise ratio
SNRC=signal to noise ratio at calibration
$O_f$=calibrated offset; and adding said correction factor $C_f$ to said receive time.

9. The method as claimed in claim 8, wherein said change in said echo pulse comprises attenuation of said echo pulse.

10. The method as claimed in claim 9, wherein said change in said echo pulse comprises a change in noise floor, and said change in noise floor changing said signal-to-noise ratio.

11. The method as claimed in claim 10, wherein said slope comprises the average slope of the leading edge of said echo pulse.

12. A level measurement device for measuring a distance to a material having a surface, said level measurement device comprising:
  a transducer for emitting energy pulses and detecting energy pulses reflected by the surface of the material;
  a controller having a receiver and a transmitter;
  said transducer having an input port operatively coupled to said transmitter and being responsive to said transmitter for emitting said energy pulses, and said transducer including an output port operatively coupled to said receiver for outputting reflected energy pulses coupled by the transducer;
  said receiver including a converter for converting said reflected energy pulses into echo signals;
  said controller including a program component for generating an echo profile based on said echo signals;
  said processing means including a program component for calculating a receive time for each of said echo signals;
  said processing means including a program component for adjusting the receive time for said echo signals in response to a change in the amplitude of said echo pulses or a change in noise floor, said program component for adjusting the receive time generating a correction factor and said correction factor being based on a signal-to-noise determination and a slope value for a leading edge of said echo pulse;
  said processing means including a program component for calculating a level measurement for the material contained in the vessel, said level measurement being based on the time between the transmission of said energy pulses and the receive time of said echo signals.

13. The level measurement device as claimed in claim 12, wherein said program component for adjusting the receive time calculates a correction factor $C_f$ as follows:

$$C_f = ((SNRC - SNR)/(S_a)) + O_f$$

where: Cf=correction factor
$S_a$=slope of an edge on said echo pulse
SNR=signal to noise ratio
SNRC=signal to noise ratio at calibration
$O_f$=calibrated offset; and said program component adds said correction factor $C_f$ to said receive time.

* * * * *